(12) United States Patent
Sekiguchi

(10) Patent No.: US 7,387,386 B2
(45) Date of Patent: Jun. 17, 2008

(54) OPHTHALMOLOGIC IMAGE PROCESSING APPARATUS

(75) Inventor: Kiyoji Sekiguchi, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 750 days.

(21) Appl. No.: 10/820,369

(22) Filed: Apr. 8, 2004

(65) Prior Publication Data

US 2004/0254477 A1 Dec. 16, 2004

(30) Foreign Application Priority Data

May 30, 2003 (JP) ............................. 2003-154312

(51) Int. Cl.
*A61B 3/14* (2006.01)
*A61B 3/10* (2006.01)
*A61B 3/02* (2006.01)

(52) U.S. Cl. .................. 351/206; 351/205; 351/222; 351/216; 351/210

(58) Field of Classification Search ................ 351/206, 351/205, 200, 208, 221, 222, 216, 210
See application file for complete search history.

(56) References Cited

U.S. PATENT DOCUMENTS

2004/0239877 A1* 12/2004 Takai ......................... 351/206

FOREIGN PATENT DOCUMENTS

JP 9-206278 8/1997

* cited by examiner

*Primary Examiner*—Ricky L Mack
*Assistant Examiner*—Brandi N Thomas
(74) *Attorney, Agent, or Firm*—Morgan & Finnegan, L.L.P.

(57) ABSTRACT

To synthesize an aperture mask having unnoticeable steps with a taken fundus image. In an image processing apparatus, taken fundus image data is inputted and then analyzed. After that, an aperture mask is selected and inputted as aperture mask data, and an image size of the fundus image compared with an image size of the aperture mask. The image size of the aperture mask is adjusted to the image size of the fundus image and then the fundus image data and the aperture mask data are developed in raster format to image memories. The image size of the fundus image is adjusted to the image size of the aperture mask based on the comparison result and a coefficient for low pass filtering process is determined according to the image size of the fundus image. After that, the degree of clearness of corresponding fundus image data is calculated based on each pixel value of the aperture mask data on which the low pass filtering process has been performed and the calculation result is outputted to the image memory. After the process is performed for all the pixels, a fundus area in the fundus image is moved to predetermined coordinates. A resultant fundus image is outputted as final image data to a storage device and a display memory and then a series of processes are completed.

9 Claims, 7 Drawing Sheets

OPHTHALMOLOGIC IMAGE PROCESSING APPARATUS

BACKGROUND OF THE INVENTION

1. Field of the Invention

The present invention relates to an ophthalmologic image processing apparatus used for ophthalmologic examination in an ophthalmologic clinic and the like.

2. Related Background Art

In a conventional fundus camera, image taking is performed with an aperture mask that performs light shielding on an area other than a central region inside a flare region located at a position immediately before an image pickup plane or at an equivalent position on an optical path, in order to determine an effective image taking area by eliminating a flare caused near a formed image, to determine a positional relationship between the image and an eye to be examined, or to determine a left or right eye in a case of picking up a pair of a papillary area and a macular area. In such fundus camera, because the aperture mask is located near an imaging plane of a fundus image, a boundary between the fundus image and the mask on the taken image is natural, so that a smooth image can be obtained.

On the other hand, there exists a fundus camera that produces a fundus image without using the aperture mask. However, the fundus image taken by such fundus camera has an unnecessary flare caused in the vicinity thereof, an image taking direction thereof cannot be checked, or left or right eye may be inadvertently determined. Therefore, when printing the images thereof, various problems may occur in the diagnostic process.

Therefore, as disclosed in Japanese Patent Application Laid-Open No. H9-206278, a method of electrically adding an aperture mask to a fundus image by synthesizing processing has been proposed. In this method, image processing for replacing a signal in an aperture mask area on the taken fundus image with data of a black level is performed. In the case where the fundus image is a video signal, the signal is changed into a signal of the black level at a display timing of the aperture mask area. In the case where the fundus image is inputted as image data, a black value is written into each pixel data in the aperture mask area.

However, performing the above-mentioned image processing to add the aperture mask causes the following problem. That is, generally, the fundus image becomes a circular image or an oval image whose top and bottom portions are chipped because an image taking object is spherical and it is preferable to perform image taking for its maximum area. Therefore, the vicinities of a horizontal portion and a vertical portion of the image become a gentle curve. However, in the case where an aperture mask process is performed on such a fundus image, an aliasing (step portion) is caused in the boundary between the aperture mask and the fundus. In particular, the aliasing becomes conspicuous in the gentle curve part of the horizontal and vertical portions, so that a region having developed the steps is very noticeable due to an extremely high contrast.

FIG. 8 is an explanatory view showing a fundus image synthesized with the aperture mask. This is an image obtained by synthesizing an aperture mask with a fundus image taken with the fundus camera using no aperture mask by a conventional method.

FIGS. 9A and 9B each show an enlarged image of a horizontal portion A and an enlarged image of a vertical portion B in the boundary region between the aperture mask and the fundus image as shown in FIG. 8. As is also apparent from the enlarged images, the boundary line between the aperture mask and the fundus image is a gentle curve. Therefore, the steps are very noticeable.

Further, a viewer may visually sense the step portion as a noise to hinder diagnosing operation. Alternatively, a viewer may feel uncomfortable with the image having the aperture mask, and this becomes a factor of a viewer's fatigue in diagnosing operation in which the viewer views several tens to several hundreds of images per day. Even in the case where the step portion is viewed through either a monitor or a printed paper, the similar influences are caused. In particular, in the case where the step portion is viewed through a monitor having a small number of pixels, the influences are noticeable.

In the case where the synthesized image is transmitted through a communication unit or subjected to JPEG compression for storage, the step portion becomes a discontinuous image. Consequently, there is a problem in that a contour in which the boundary portion between the fundus image and the aperture mask appears somewhat bright develops. A false color is generated in the portion which appears bright and it is a color which is not included in the original fundus image, so that attention is required for diagnosis. In order to suppress the generation of the false color, it is necessary to reduce the degree of compression, which means that it is useless to perform the compression. Further, because the step portion has a large number of harmonic components, there is a problem in that the compression efficiency is reduced.

SUMMARY OF THE INVENTION

As described above, there is the case where defects are caused in synthesizing an aperture mask with a fundus image in the conventional ophthalmologic image processing apparatus. Thus, various measures against the defects are desired.

The present invention has been made in view of the above-mentioned problems. Therefore, an object of the present invention is to provide an ophthalmologic image processing apparatus that produces a synthesized image with less sense of discomfort in synthesizing process for synthesizing a fundus image with an aperture mask image.

According to the present invention, there is provided an ophthalmologic image processing apparatus that masks a fundus image using an aperture mask image, including:

input means for inputting the fundus image;

image generation means for generating an aperture mask image in accordance with information of the fundus image or inputting the aperture mask image;

image adjustment means for adjusting a value of the fundus image; and synthesizing means for synthesizing the fundus image whose value is adjusted with the aperture mask image, in which the image adjustment means adjusts the value of the fundus image based on coordinates in a boundary between a mask area of the aperture mask image and an area of the fundus image.

Other objects, features and advantages of the present invention will be apparent from the following description taken in conjunction with the accompanying drawings, in which like reference characters designate the same or similar parts throughout the figures thereof.

BRIEF DESCRIPTION OF THE DRAWING

The accompanying drawings, which are incorporated in and constitute a part of the specification, illustrate embodiments of the invention and, together with the descriptions, serve to explain the principle of the invention.

DETAILED DESCRIPTION OF THE PREFERRED EMBODIMENTS

The present invention will be described in detail with reference to an embodiment shown in FIGS. 1 to 7.

Figure 1:
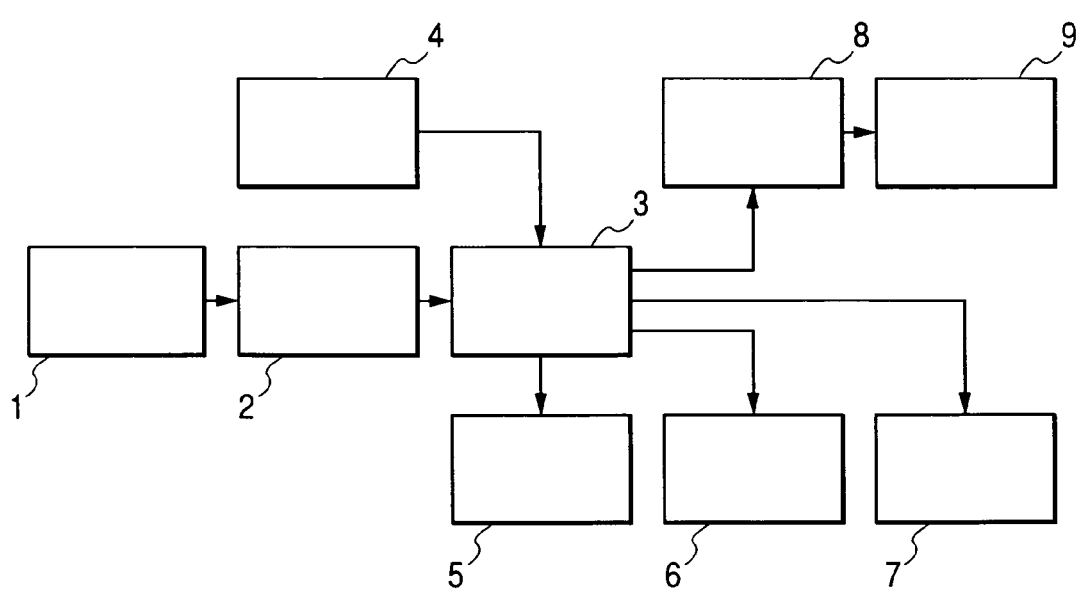
FIG. 1 is a block circuit structural diagram showing an embodiment of the present invention.

FIG. 1 is a block circuit structural diagram showing a fundus image processing apparatus according to an embodiment of the present invention. A fundus camera unit 1 is composed of a device that projects image taking light to a fundus and forms a reflection image with the light reflected from the fundus onto an image pickup device. The fundus camera unit 1 is a unit which includes an optical system, a mechanism, and an electrical unit, which are known, and takes an image of the fundus of a person to be examined to generate fundus image data. An output of the fundus camera unit 1 is inputted to an image processing apparatus 3 through an input interface 2 that inputs the fundus image data. An aperture mask input unit 4 that inputs an aperture mask image is connected with the image processing-apparatus 3.

An output of the image processing apparatus 3 is connected with a first image memory 5, a second image memory 6, a storage device 7, and a display memory 8. An output of the display memory 8 is connected with a display device 9.

Figure 2:
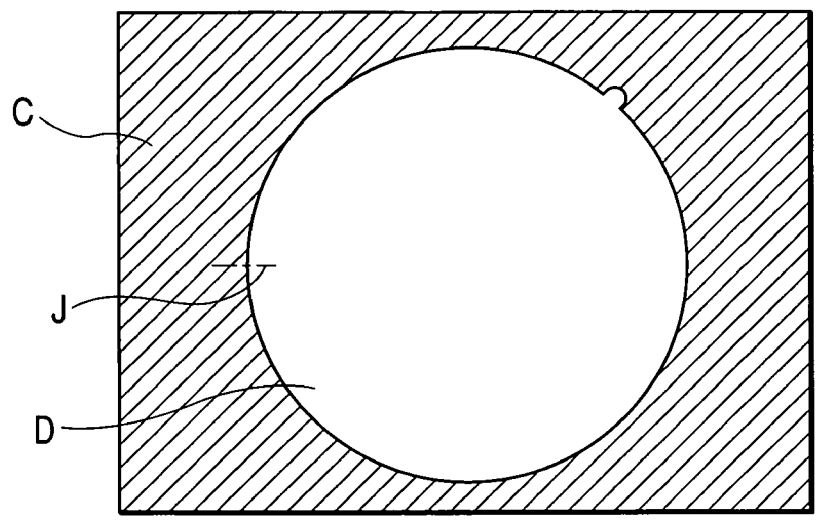
FIG. 2 is an explanatory view showing an aperture mask.

FIG. 2 is an explanatory view showing the aperture mask image included in the aperture mask input unit 4. In FIG. 2, a region C is a region for masking the fundus image data and a region D is a region for outputting the fundus image data without masking it.

Figure 3:
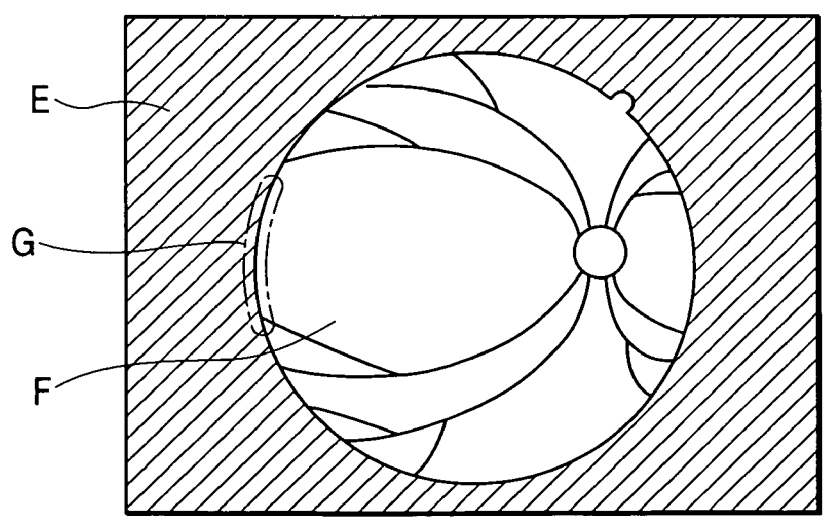
FIG. 3 is an explanatory view showing a fundus image on which a synthesizing process has been performed.

FIG. 3 shows a fundus image synthesized with the aperture mask. In FIG. 3, a mask area E indicates a masked image portion, a fundus image region F indicates a fundus image which is not masked, and a boundary region G indicates a boundary portion between the aperture mask and the fundus image.

Figure 4A:
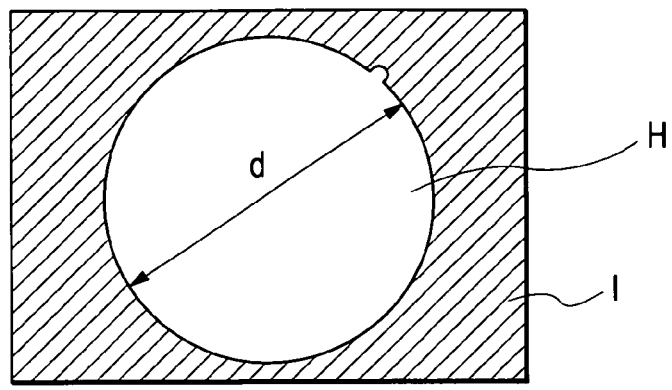
FIGS. 4A, 4B, and 4C are explanatory views showing different kinds of aperture masks.
Figure 4B:
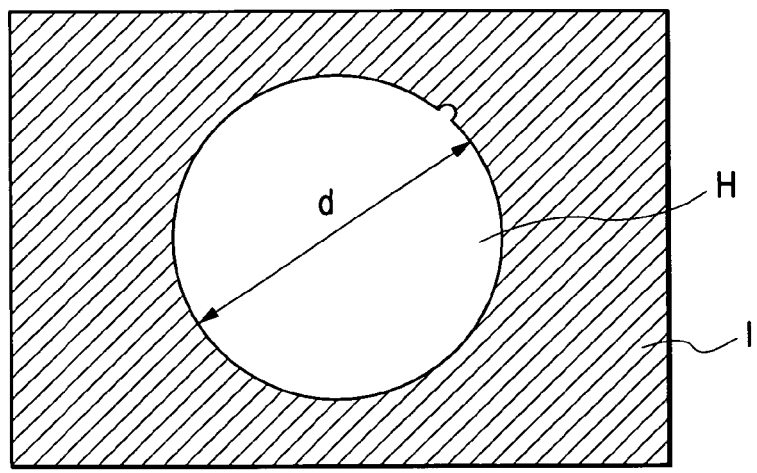
Figure 4C:
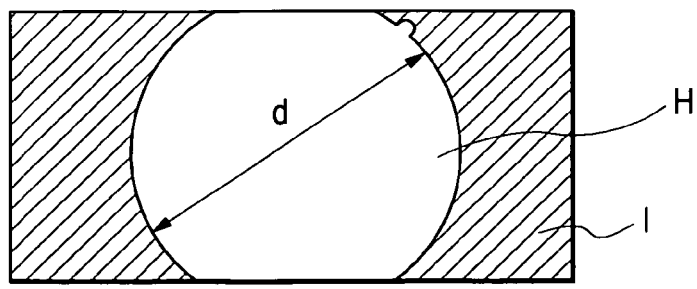

FIGS. 4A to 4C are explanatory views showing aperture masks, in which a fundus image region H having a diameter of d is an area in which an image is picked up by the fundus image unit 1. As shown in FIGS. 4A to 4C, a size of a mask area I around the fundus image region H is changed according to an image pickup plane. In other words, with respect to an aspect ratio of the taken fundus image, there are, for example, three types as shown in FIGS. 4A to 4C, so that an aperture mask image corresponding to each type is required. Therefore, aperture mask images corresponding to plural sizes are stored in the aperture mask input unit 4.

Even in the case where the same image pickup unit (fundus camera unit) is used, an image size of a fundus image can be changed when it is outputted. In this case, because the aspect ratio of the fundus image is identical, the type of aperture mask is selected according to the image size of the fundus image. Therefore, even in the case where the fundus image is enlarged or reduced, a size of the aperture mask can be adjusted to the image size of the fundus image. The aperture mask input unit 4 may be constructed such that aperture mask images are prepared in advance according to the image pickup unit to be used, and an aperture mask image is selected based on an image size of an inputted fundus image. Alternatively, the aperture mask input unit 4 may be constructed such that a ratio between the image size of the fundus image and a size of a fundus portion thereof and a position of the fundus portion are set as numeral value information, and an aperture mask image is automatically generated based on the image size of the inputted fundus image.

Figure 5:
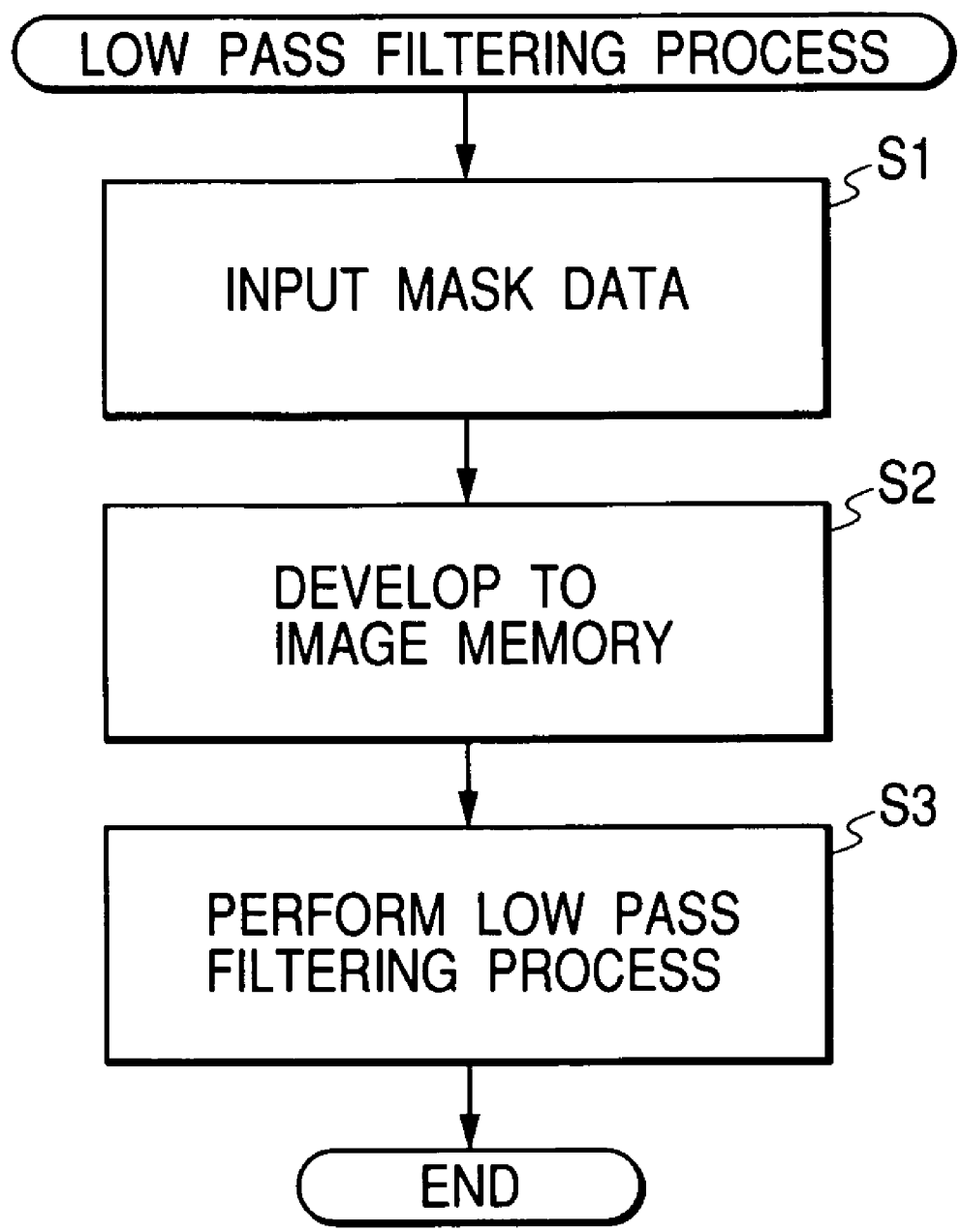
FIG. 5 is a flow chart showing a low pass filtering process.

FIG. 5 is a flow chart in the case where a low pass filtering process is performed on the aperture mask. First, in Step S1, aperture mask data is inputted to the image processing apparatus 3. Then, in Step S2, the aperture mask data is developed to the image memories 5 and 6. Subsequently, in Step S3, the low pass filtering process is performed on the aperture mask data and then the aperture mask data is stored in the storage device 7. Even in the case where plural kinds of aperture masks are used, the same process is performed to store the aperture mask data.

In the case where the process is performed in advance, when the image size of the aperture mask image is equal to the image size of an inputted fundus image, it is possible to perform the process speedily.

Figure 6:
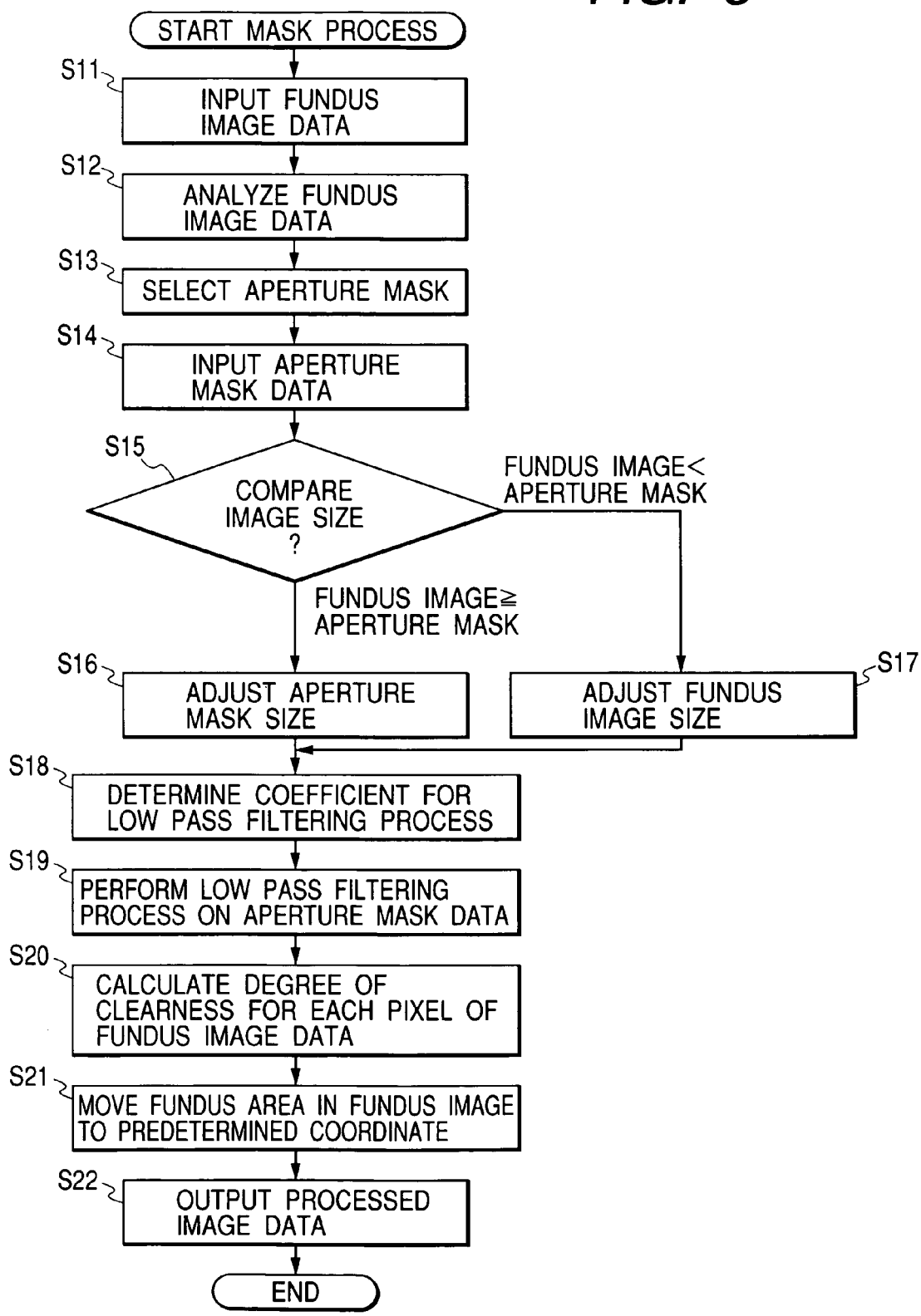
FIG. 6 is a flow chart showing an aperture low pass filtering process.

FIG. 6 is a flow chart showing an aperture mask process. First, in Step S11, the fundus image data taken by the fundus camera unit 1 is inputted. Then, in Step S12, header information of the inputted fundus image data is analyzed to obtain the number of color bits and the image size thereof. Next, in Step S13, an aperture mask is selected based on the obtained image size of the fundus image. In Step S14, the aperture mask selected in Step S13 is inputted as aperture mask data.

Subsequently, in Step S15, the image size of the fundus image is compared with the image size of the aperture mask image. When the image size of the fundus image is equal to or larger than the image size of the aperture mask image, the process goes to Step S16. On the other hand, when the image size of the fundus image is smaller than the image size of the aperture mask image, the process goes to Step S17.

In Step S16, the image size of the aperture mask image is adjusted to the image size of the fundus image, and then the fundus image data and the aperture mask data are developed in raster format to the first image memory 5 and the second image memory 6, respectively. The fundus image data is converted into a 24-bit color (24 bits are allocated for a pixel.) and divided into respective colors of R, G, and B for development. In addition, the aperture mask data is developed using an 8-bit (8 bits are allocated for a pixel.) gray scale in raster format according to a gradation of the fundus image data. In Step S17, the image size of the fundus image is adjusted to the image size of the aperture mask, and then the same process is performed for raster development.

Subsequently, in Step S18, a coefficient for the low pass filtering process is determined according to the image size of the fundus image. In the case where the image size of the fundus image is large, the degree of the low pass filtering or the repetition number of filtering process is increased. Therefore, a slope of the boundary region between the aperture mask and the fundus image can be made gentle. However, in the case where the image size is small, the development of the slope is alleviated, thereby reducing the number of blurred fundus image.

In Step S19, the low pass filtering process is performed on the aperture mask data. When the low pass filtering process is performed on the aperture mask data, even in the case where any of aperture masks as shown in FIGS. 4A to 4C is used, an effect caused by the low pass filtering process appears along a boundary line between the fundus image region H having the diameter of d and the mask area I. Therefore, the boundary line becomes a blur state.

In Step S20, the degree of clearness of corresponding fundus image data is calculated based on each pixel value of the aperture mask data on which the low pass filtering process has been performed and the calculation result is outputted to the second image memory 6. After the process is performed for all pixels of the fundus image, the fundus area in the fundus image is moved to predetermined coordinates in Step S21. This is because the masked black region is used as a region for displaying or printing image taking information and patient information. Note that, if it is unnecessary to move the fundus area, this processing step can be skipped. In Step S22, the final image data is outputted to the storage device 7 and the display memory 8 and then a series of processes are completed.

Figure 7:
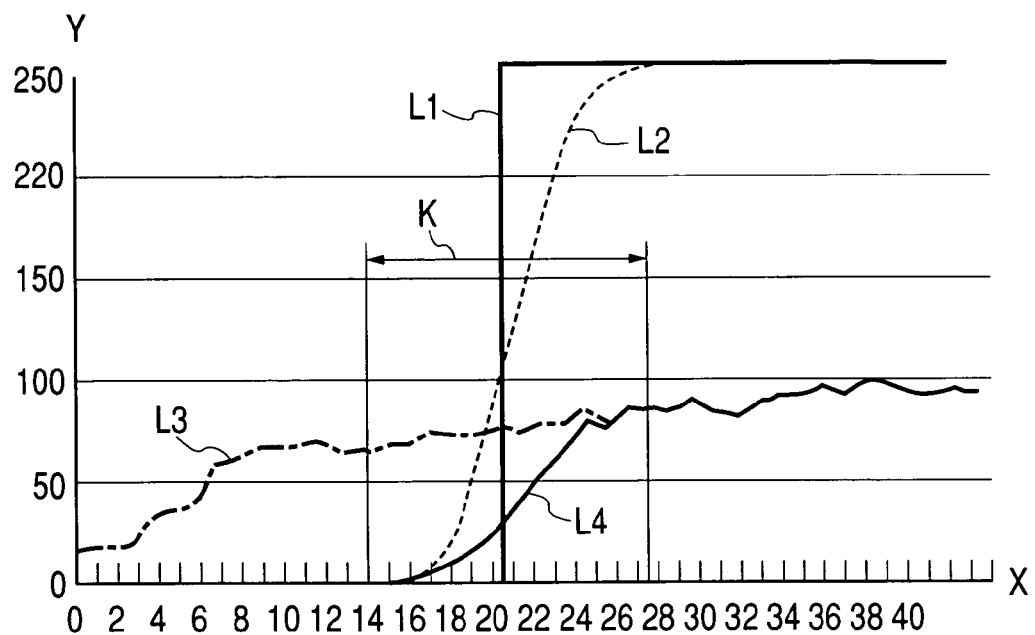
FIG. 7 is an explanatory view showing an aperture mask synthesizing process.
Figure 8:
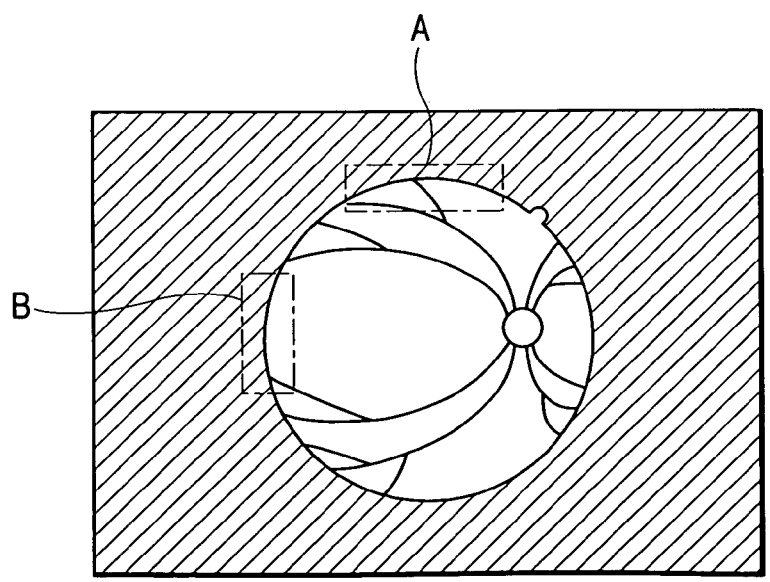
FIG. 8 is an explanatory view for Related Background Art.
Figure 9A:
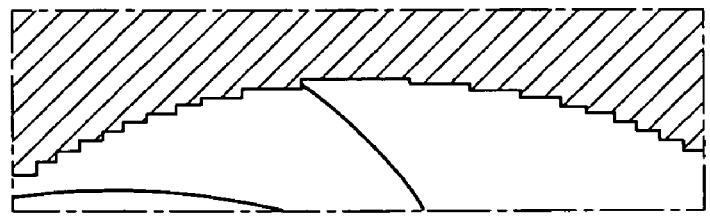
FIGS. 9A and 9B are enlarged views showing step portions in Related Background Art.
Figure 9B:
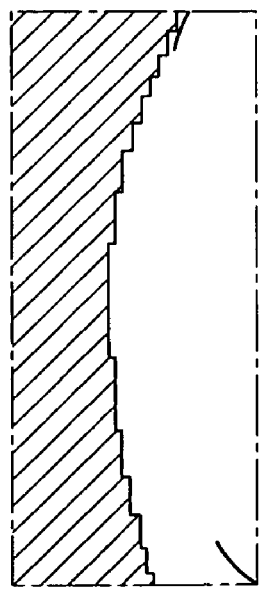

FIG. 7 is an explanatory view showing a process for synthesizing the aperture mask data with the fundus image data. In FIG. 7, an X-coordinate indicates a pixel coordinate on a line of a horizontal portion J which is the boundary between the fundus image and the aperture mask as shown in FIG. 2. In addition, a Y-coordinate indicates each pixel data. The aperture mask data, the fundus image data, and synthesized data are overlapped with each other to obtain a graph.

In FIG. 7, a line L1 indicates aperture mask data on which the low pass filtering process is not performed. As shown by the line L1, data is 0 in the region C indicated by an oblique line in FIG. 2 and changed from the left in the right direction, and a value of that data becomes 255 at the boundary portion between the aperture mask data and the fundus image data on the horizontal portion J.

A line L2 indicates aperture mask data on which the low pass filtering process has been performed and is a gentle curve joining data of 0 to data of 255. This image data has a gray scale. Therefore, the black data gradually becomes a gray and further gradually becomes white.

A line L3 indicates an example of G-color data of RGB colors of the fundus image data corresponding to the region D shown in FIG. 2. The intensity gradually increases from the left to the right direction. The calculation using the data of the line L2 and the data of the line L3 is performed by the following expression to obtain an output image. This process (calculation) is performed on each of the RGB color data.

Output data=(line $L3$ data)·(line $L2$ data+1)/256

A line L4 indicates pixel data of a fundus image on which synthesizing process has been performed. An interval K indicates a width of a slope portion of the aperture mask on which the low pass filtering process has been performed. In the case where the coefficient for the low pass filtering process or the number of processes is increased, the width of the slope portion extends.

When the fundus image data on which synthesizing process has been performed is stored in the storage device 7, the aperture mask image may be binary data or the 8-bit data as indicated by the line L1 in FIG. 7.

According to the above-mentioned expression, after the completion of the low pass filtering process, the black data (=0) is outputted in the region in which the data of the line L2 is 0. The fundus image data is outputted as it is in the region in which the data of the line L2 is 255. The fundus image data whose intensity is reduced is outputted with reducing the value of the line L2. In the case where such process is performed, the steps in the boundary region between the aperture mask and the fundus image are unnoticeable, thereby obtaining a uniform image with a small visible noise. Therefore, the fundus image data in which the steps in the boundary region between the aperture mask and the fundus image are unnoticeable can be produced. In particular, in the case where diagnosis is performed using a monitor or a printed output, as compared with a conventional image, the steps are unnoticeable and a visible noise is small. Thus, a fatigue of the viewer can be reduced and diagnosing operation can be efficiency performed. In the case where the produced image is compressed again for storage or transmission to another location, an unnecessary harmonic component in the image can be removed, so that a compression size can be reduced, a compression time can be shortened, and storage efficiency and communication efficiency can be improved.

The above-mentioned processing is performed on each of the RGB images but the following may be alternately performed. That is, the RGB data is converted into YUV data; the above-mentioned processing is performed on Y-data serving as intensity data; and then, the YUV data is converted into the RGB data.

In the case where the fundus camera unit 1 is specified and only the image size is changed, Step S13 (aperture mask selection), Step S14, and Step S17 shown in FIG. 6 can be omitted and the aperture mask may be reduced in size according to the size of an inputted fundus image. In the case where the size of the fundus image is larger than a certain size, the low pass filtering process in Step S18 can be fixed. In the case where the aperture mask image processed in advance as shown in FIG. 5 is used, a processing speed can be improved.

An ophthalmologic image processing apparatus that produces a synthesized image with less sense of discomfort in synthesizing processing for synthesizing the fundus image with the aperture mask image as described above can be provided.

It is needless to say that the object of the present invention is accomplished by providing to a system or an apparatus a storage medium in which a program code of software which realizes the functions of an apparatus or a system according to the embodiment is stored, and causing a computer (CPU, MPU, or the like) of the apparatus or the system to read out the program code stored on the storage medium and execute the program code.

In this case, the program code itself read out from the storage medium realizes the function of the embodiment, and thus the storage medium on which the program code is stored and the program code constitute the present invention.

A ROM, a floppy (registered trademark) disk, a hard disk, an optical disk, a magneto-optical disk, a CD-ROM, a CD-R, a magnetic tape, a nonvolatile memory card, or the like can be used as the storage medium for supplying the program code.

Further, it is needless to say that the scope of the present invention includes not only the case where the function of the embodiment is implemented by executing a program code read out by a computer but also the function of the embodiment is accomplished by causing an OS or the like which operates on the computer to perform a part or all of the actual operations based on instructions of the program code.

Further, it is needless to say that the scope of the present invention includes the case where the function of the embodiment is accomplished by writing the program code read out from the storage medium into a memory which is provided on a functional expansion board inserted into a computer or in a functional expansion unit connected to the computer and then causing a CPU or the like provided in the functional expansion board or the functional expansion unit to perform a part or all of the actual operations based on instructions of the program code.

In the case where the present invention is applied to such a program or a recording medium in which the program is stored, the program is composed of, for example, program codes corresponding to the flow chart shown in FIG. 6 as described above.

What is claimed is:

1. An ophthalmologic image processing apparatus that masks a fundus image using an aperture mask image, comprising:
    input means for inputting the fundus image;
    image generation means for generating an aperture mask image in accordance with information of the fundus image or inputting the aperture mask image;
    image adjustment means for adjusting a value of the fundus image, wherein the image adjustment means comprises a smoothing means for performing a low pass filtering process on the aperture mask image, and the image adjustment means adjusts the value of the fundus image in accordance with a pixel value of the aperture mask image on which the pass filtering process is performed; and
    synthesizing means for synthesizing the fundus image whose value is adjusted with the aperture mask image,
    wherein the image adjustment means adjusts the value of the fundus image based on coordinates in a boundary between a mask area of the aperture mask image and an area of the fundus image.

2. An apparatus according to claim 1, wherein the image adjustment means reduces a pixel value from the boundary between the mask area of the aperture mask image and the region of the fundus image to an outside of the mask area and increases the pixel value from the boundary to the inside of the mask area.

3. An apparatus according to claim 1, wherein the image adjustment means adjusts the value of the fundus image by multiplying the fundus image by a coefficient proportional to the pixel value of the aperture mask image on which the pass filtering process is performed.

4. An apparatus according to claim 1, wherein the image generation means comprises comparison means for comparing a size of the fundus image with a size of the aperture mask image, and
    the image generation means adjusts the size of the aperture mask image in accordance with a comparison result of the comparison means.

5. An apparatus according to claim 1, wherein the image generation means comprises selection means for selecting one of the aperture mask images in accordance with a size of the fundus image.

6. An apparatus according to claim 1, wherein a number of bits of a gray scale of the aperture mask image is different from a number of bits of one pixel for the fundus image.

7. An apparatus according to claim 1, wherein the smoothing means adjusts a degree of the low pass filtering process in accordance with a size of the fundus image when the low pass filtering process is performed.

8. An apparatus according to claim 1, wherein the image adjustment means comprises moving means for moving a fundus area in the fundus image whose value is adjusted to predetermined coordinates on the fundus image.

9. An ophthalmologic image processing method that masks a fundus image using an aperture mask image, comprising:
    an inputting step of inputting the fundus image;
    an image generating step of generating an aperture mask image in accordance with information of the fundus image or inputting the aperture mask image;
    an image adjusting step of adjusting a value of the fundus image, wherein the image adjusting step comprises performing a low pass filtering process on the aperture mask image; and adjusting the value of the fundus image in accordance with a pixel value of the aperture mask image on which the pass filtering process is performed; and
    a synthesizing step of synthesizing the fundus image whose value is adjusted with the aperture mask image,
    wherein in the image adjusting step, the value of the fundus image is adjusted based on coordinates in a boundary between a mask area of the aperture mask image and an area of the fundus image.

* * * * *

UNITED STATES PATENT AND TRADEMARK OFFICE
CERTIFICATE OF CORRECTION

PATENT NO. : 7,387,386 B2  Page 1 of 1
APPLICATION NO. : 10/820369
DATED : June 17, 2008
INVENTOR(S) : Kyoji Sekiguchi It is certified that error appears in the above-identified patent and that said Letters Patent is hereby corrected as shown below:

On the cover page, item (75) Inventor:

Please replace "Kiyoji Sekiguchi" with --Kyoji Sekiguchi--.

On the cover page, section (56) References Cited:

Add a subsection heading --OTHER PUBLICATIONS--;

Under the subsection heading --OTHER PUBLICATIONS--, add the following references:

Jon Y. Hardeberg, "Digital Red Eye Removal", Journal of Imaging Science and Technology, Volume 46, July/August 2002.

European Search Report dated October 5, 2004.

Signed and Sealed this

Ninth Day of December, 2008

JON W. DUDAS
*Director of the United States Patent and Trademark Office*